US007804736B2

(12) United States Patent
Alexandru

(10) Patent No.: US 7,804,736 B2
(45) Date of Patent: Sep. 28, 2010

(54) DELAY CONTROLLER FOR ULTRASOUND RECEIVE BEAMFORMER

(75) Inventor: Radu Alexandru, Cheshire, CT (US)

(73) Assignee: Aloka Co., Ltd., Tokyo (JP)

( * ) Notice: Subject to any disclaimer, the term of this patent is extended or adjusted under 35 U.S.C. 154(b) by 1217 days.

(21) Appl. No.: 11/395,863

(22) Filed: Mar. 30, 2006

(65) Prior Publication Data
US 2007/0232906 A1 Oct. 4, 2007

(51) Int. Cl.
*A61B 8/00* (2006.01)
*G03B 42/06* (2006.01)

(52) U.S. Cl. ......................................................... 367/11
(58) Field of Classification Search ................... 367/11; 600/437, 447
See application file for complete search history.

(56) References Cited

U.S. PATENT DOCUMENTS

| 5,653,236 | A * | 8/1997 | Miller ........................ 600/447 |
| 6,217,516 | B1 * | 4/2001 | Poland et al. ................ 600/447 |
| 7,508,737 | B1 * | 3/2009 | Alexandru .................. 367/103 |
| 2007/0232906 | A1 * | 10/2007 | Alexandru .................. 600/437 |
| 2007/0239013 | A1 * | 10/2007 | Alexandru .................. 600/443 |
| 2008/0262351 | A1 * | 10/2008 | Scampini ...................... 367/7 |

OTHER PUBLICATIONS

Van Aken, "An Efficient Ellipse-Drawing Algorithm", IEEE Computer Graphics and Applications Magazine, vol. 4, No. 9, pp. 24-35 (Sep. 1984).
Ki Jeon et al., "An Efficient Real-Time Focusing Delay Calculation in Ultrasonic Imaging Systems", Ultrasonic Imaging, 16, pp. 231-248 (1994).
H. Feldkamper et al., "Low Power Delay Calculation for Digital Beamforming in Handheld Ultrasound Systems", Proc. IEEE Ultrason. Symp. 2, pp. 1763-1766 (2000).
B. Tomov and J. Jensen, "Delay Generation Methods with Reduced Memory Requirements", Proc. SPIE, vol. 5035, pp. 491-500 (2003).

* cited by examiner

*Primary Examiner*—Dan Pihulic
(74) *Attorney, Agent, or Firm*—Buckley, Maschoff & Talwalkar LLC

(57) ABSTRACT

An ultrasound system includes an ultrasound transducer having an array of elements and a beam origin located between two adjacent elements, each of the elements for converting received energy into an echo signal; and a beamformer that includes an initialization controller having initialization controller circuitry for calculating initialization parameters according to a process for calculating initialization parameters from a reduced table; at least one channel having a delay circuit and a delay controller; and a summer for summing phase-aligned signals to form a beamformed signal.

28 Claims, 4 Drawing Sheets

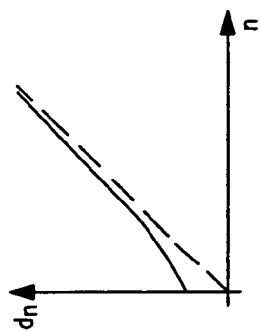
FIG. 2
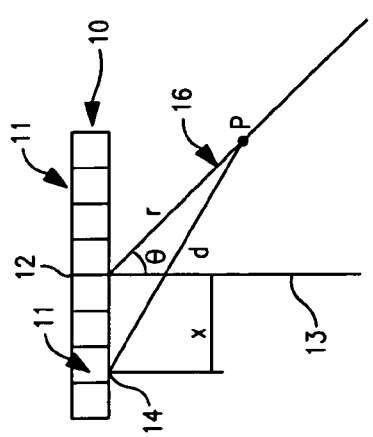
FIG. 1
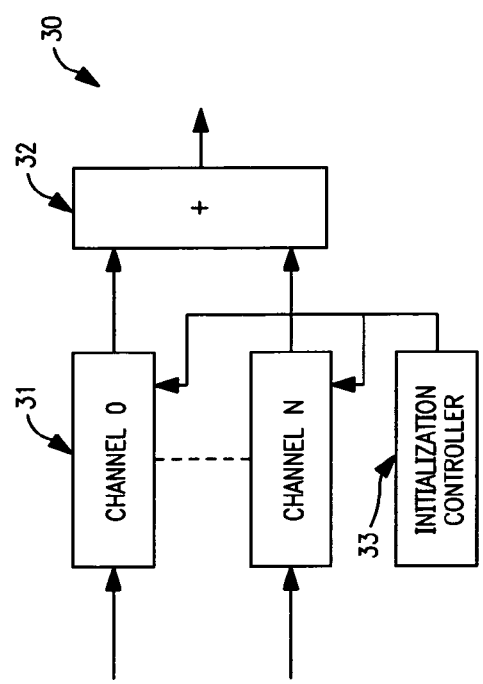
FIG. 3A
FIG. 3

DELAY CONTROLLER FOR ULTRASOUND RECEIVE BEAMFORMER

FIELD OF THE INVENTION

The present invention relates to ultrasound imaging and, more particularly, relates to the focusing of received ultrasound beams for ultrasound imaging.

BACKGROUND OF THE INVENTION

In ultrasound imaging, a transducer is used to transmit ultrasound beams into the medium to be examined, for example, a region of the human body; receive the ultrasound echoes reflected from various discontinuities in the medium; and, transform the reflected ultrasound echoes into electrical signals. The electrical signals then undergo a number of processing steps and are eventually transformed into an image which can be displayed on a device such as a cathode ray tube or printed in order to be examined by a physician.

Ultrasound transducers typically consist of arrays of small rectangular piezoelectric elements. A subset of such elements used to transmit or receive an ultrasound beam is called a transmit or receive aperture, respectively. Typically, the geometrical centers of transmit and receive apertures coincide, and the ultrasound beam(s) are represented as linear beam axes originating at the center of the apertures.

The receive operation is performed by a multi-channel receive beamformer. The multi-channel receive beamformer applies delays and weights to the signals received by various receive aperture elements and sums them to obtain focused signals along the desired beam axis. The purpose of the delays is to compensate for the difference in arrival time caused by difference in propagation paths from the point of interest of the medium to the different elements of the aperture. In order to obtain ultrasound beams focused at multiple depths along the beam axis, the receive delays are varied with depth such that all the signals which are summed to obtain the echo from a point on the beam axis arrive from that same point. This is called dynamic receive focus, and the image quality is critically dependent on the accuracy of the dynamic receive delays or equivalently of the echo arrival time. It is known in the art that a delay accuracy of $1/32\, F_c$ is desirable, where $F_c$ is the center frequency of the transducer's frequency characteristic.

The received signals can be delayed by various methods, for example, analog and digital, but in all cases a delay, or arrival time, controller has to produce the desired delay control signals. Practical beamformers use circuits which calculate the dynamic delays in real time starting from a small number of pre-calculated initialization parameters. One such circuit is based on a computer graphics algorithm introduced in an article by Van Aken entitled, "An efficient ellipse-drawing algorithm", IEEE Computer Graphics and Applications Magazine, vol. 4, no. 9, pp. 24-35 (September 1984), and adapted to ultrasound imaging as described in an article by Ki Jeon et al., "An efficient real-time focusing delay calculation in ultrasonic imaging systems", Ultrasonic Imaging, 16, pp. 231-248 (1994). Variants of and improvements to this delay generation method are described in U.S. Pat. No. 5,669,384 to Park et al. entitled, "Real time digital reception focusing method and apparatus adopting the same"; U.S. Pat. No. 5,836,881 to Bae entitled "Focusing delay calculation method for real-time digital focusing and apparatus adopting the same"; "Low power delay calculation for digital beamforming in handheld ultrasound systems", H. Feldkamper et. al., Proc. IEEE Ultrason. Symp. 2, pp. 1763-1766 (2000); "Delay generation methods with reduced memory requirements", B. Tomov and J. Jensen, Proc. SPIE, Vol. 5035, pp. 491-500 (2003); and U.S. Pat. No. 5,724,972 to J. Petrofsky, entitled "Method and apparatus for distributed focus control with slope tracking". In general these methods calculate the desired quantity (arrival time/delay) iteratively from one depth to the next by adding/subtracting to/from the quantity either a non-zero or a zero value depending on the sign of a decision quantity which is also calculated iteratively.

A first shortcoming of these prior art delay generation methods is their limited accuracy. The original method's error may be up to one half of the sampling period $T=1/F$, where F is the sampling frequency. In ultrasound imaging F is typically four times the center frequency ($F=4\, F_c$). This results in accuracy of $1/8\, F_c$, 4 times worse than the desired $1/32\, F^c$. The prior art methods mentioned above attempt to improve on this result by combining, for example, increasing the sampling rate and increasing the algorithm complexity (and therefore the circuit complexity), both of which are undesirable as is recognized by one of ordinary skill in the art.

A second shortcoming of these prior art methods is the relatively large number of initialization parameters, that is, at least 2 parameters for each array element and each beam direction. For a typical phased array with 128 elements, 256 initialization parameters are required per beam direction.

Therefore, a method and circuit for calculating the delay or the arrival time with an accuracy of at least $1/32\, F_c$ at a sampling rate $4\, F_c$, and with a reduced number of initialization parameters is required.

SUMMARY OF THE INVENTION

In accordance one aspect of the present invention, in an ultrasound imaging system broadly comprising an ultrasound transducer having an array of elements and a beam origin located between two adjacent elements, each element for converting received energy into an echo signal, a process for calculating a timing function, the process broadly comprising the steps of calculating for a first left element and a first right element a distance ($d_n$) at integer-valued depth (n), said distance ($d_n$) measured from said beam origin to a point on a beam axis of an ultrasound beam; estimating a distance ($\hat{d}_n$) measured from a center of the first left element and the first right element to the point on the beam axis; adding the distance ($\hat{d}_n$) to the integer-valued depth (n) to generate an arrival time; subtracting the distance ($\hat{d}_n$) from the integer-valued depth (n) to generate a delay; adding a constant ($C_2$) to the arrival time; and adding a constant ($C_1$) to the delay.

In accordance with another aspect of the present invention, an ultrasound system broadly comprising an ultrasound transducer comprising an array of elements and a beam origin located between two adjacent elements, each of the elements for converting received energy into an echo signal; and a beamformer broadly comprising an initialization controller including initialization controller circuitry for calculating initialization parameters; at least one channel including a delay circuit and a delay controller for calculating a timing function according to the process of claims 1-7; and a summer for summing phase-aligned signals to form a beamformed signal.

In accordance with yet another aspect of the present invention, in an ultrasound imaging system broadly comprising an ultrasound transducer having an array of elements and a beam origin located between two adjacent elements, each element for converting received energy into an echo signal, a process for calculating initialization parameters from a reduced parameter table, the process broadly comprising the steps of setting at least one increment value for at least one initialization parameter for a first left element located to the left of the beam origin and a first right element located to the right of the beam origin; storing in a memory storage device the at least one increment for the first left element and the first right element; calculating the at least one initialization parameter for at least one beam steering angle for the first left element and for the first right element; storing in the memory storage device the at least one initialization parameter for the first left element and the first right element; and calculating at least one additional initialization parameter for the at least one beam steering angle for at least one next left element located to the left of the first left element and for at least one next right element located to the right of the first right element based upon the stored at least one initialization parameter for the first left element and the first right element.

In accordance with yet another aspect of the present invention, an ultrasound system broadly comprises an ultrasound transducer broadly comprising an array of elements and a beam origin located between two adjacent elements, each of the elements for converting received energy into an echo signal; and a beamformer broadly comprising an initialization controller including initialization controller circuitry for calculating initialization parameters according to the process of claims 15-23; at least one channel including a delay circuit and a delay controller; and a summer for summing phase-aligned signals to form a beamformed signal.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIG. 1 illustrates the geometry used to calculate the echo arrival time in phased array imaging;

FIG. 2 shows the relationship between depth along the beam axis and distance from the point on the beam axis to the center of the receiving element for the center element and an element situated away from the center of the aperture;

FIG. 3 shows the block diagram of a typical receive beamformer;

FIG. 3a show the general block diagram of a beamformer channel;

Like reference numbers and designations in the various drawings indicate like elements.

DETAILED DESCRIPTION OF THE INVENTION

Figure 4:
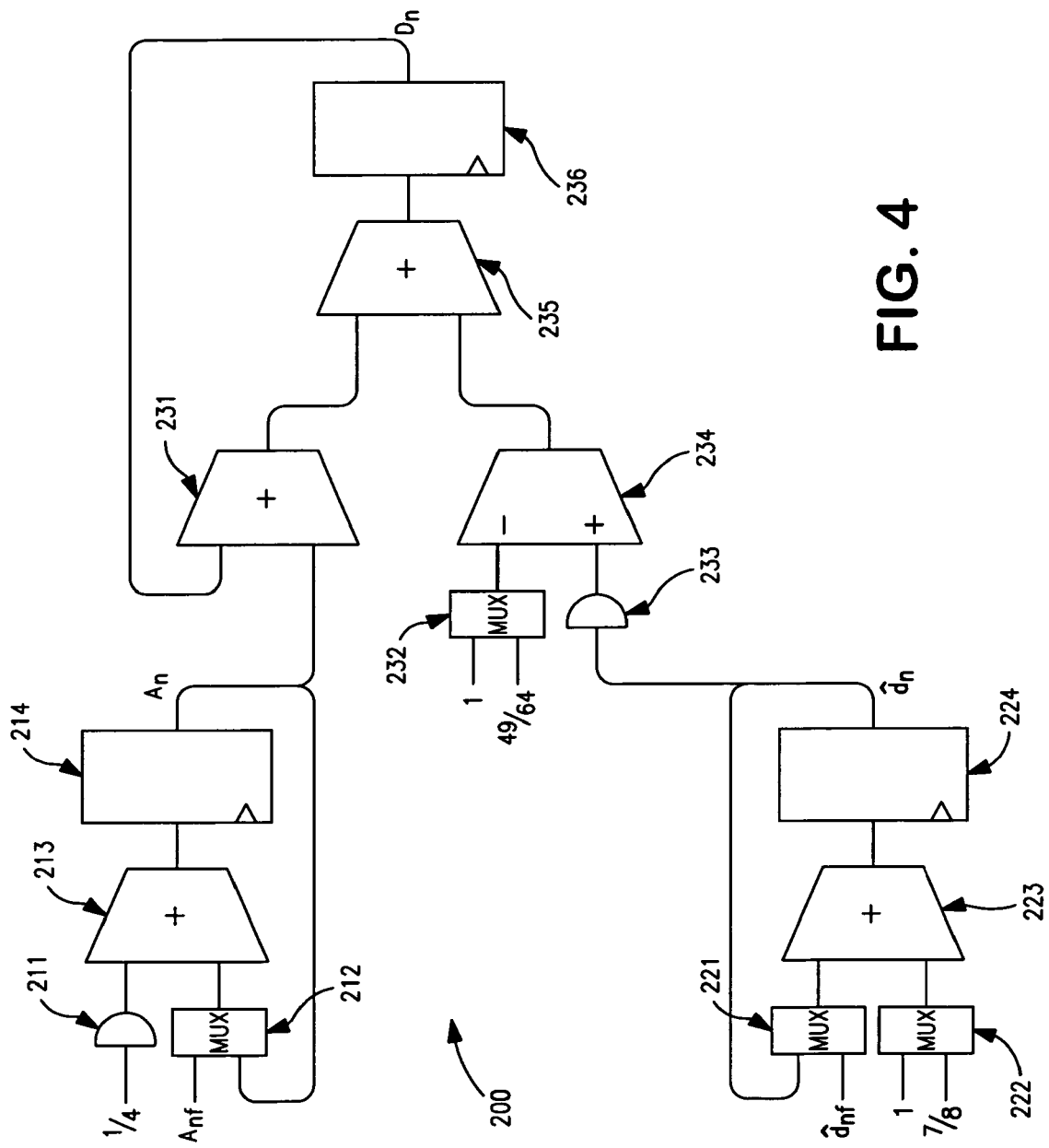
FIG. 4 shows a circuit which calculates the distance from points on the beam axis to the center of an element according to the method of the invention.

It has been discovered using simulation that for most imaging geometries used in medical ultrasound imaging, when the focus point moves by a distance $\Delta$ down the beam axis, the distance from the focus point to an aperture element increases by anywhere from $(1-\frac{1}{2}^i)\Delta$ to $\Delta$, where i is an integer in the range 2 to 4. This finding leads to algorithms which calculate the echo arrival time or the delay for each depth position iteratively, adding one of the two constants $(1-\frac{1}{2}^i)\Delta$ or $\Delta$ depending on a decision criterion which is also iteratively calculated. The delay error or arrival time error of the method of the present invention is less than $\frac{1}{8}$ of the sampling period. The algorithm of the present invention involves only simple mathematical operations, that is, additions and subtractions. Variants of the method of the present invention that produce even greater accuracy and no increase, or a small increase, in complexity are also described herein.

The initialization parameters of the proposed method(s) of the present invention are proportional with the distance of each element to the center of the array. This allows generating the initialization parameters for all elements using simple mathematical calculations starting from a reduced number of only 4 parameters for each beam direction.

Referring now to FIG. 1, a phased array 10 may contain a center element 12 and at least one element 11 to the left and to the right of the center element 12. Each element 11 includes a center 14 located at a distance x from the center element 12. Since phased arrays typically possess an even number of elements and the true center falls between two elements 11, the center element 12 is theoretical for purposes of explanation. A vertical axis 13 is shown for the purpose of providing a frame of reference, e.g., a Cartesian coordinate system. Theoretically, an ultrasound beam may originate from an aperture (not shown) of the array center 12 and travel a distance r to a point P as shown in FIG. 1. The ultrasound beam may then reflect off a media (not shown) and travel a distance d to the center 14 of an element 11. The center 14 of element 11 may be situated at a coordinate x relative to the vertical axis 13. The ultrasound beam from array center 12 to point P may be referred to as a beam axis 16. The beam axis 16 may be steered at an angle $\theta$ relative to the vertical axis 13. In this example, the value of x would be negative. Using the distances r and d and the angle $\theta$, the arrival time of an echo from point P on the beam axis 16 to element 11 of the phased array 10 may be calculated by one of ordinary skill in the art.

The total travel time, or the arrival time, of the ultrasound beam through the media is shown below in Equation (1):

$$t=(r+d)/c \quad (1)$$

where t is the total travel time of the ultrasound beam; r is the distance from the array center aperture to Point P; d is the distance from Point P to an element center; and, c is the velocity of the ultrasound beam.

For beamforming applications, t has to be evaluated for discrete values of r at intervals $\Delta r$ using an Equation (2) provided below:

$$\Delta r=cT/2 \quad (2)$$

where $\Delta r$ is the 2-way travel time along the beam axis 16 between two sampling times; T is a unit of time; and, c is the velocity of the ultrasound beam.

We choose T=1/F as a unit of time and cT/2 as a unit of distance the ultrasound beam travels in two directions, i.e., forward and reflection, in an amount of time T. With these units r takes integer values n=0, 1, ... and t takes the values as shown below in Equations (3) and (4):

$$t_n=(n+d_n)/2 \quad (3)$$

where $$d_n=\sqrt{n^2+x^2-2nx\sin\theta} \quad (4)$$

wherein $t_n$ is the arrival time; n is the distance from the array center aperture to Point P as measured as an integer value; $d_n$ is the distance from Point P to an element center; and, x is the distance from the center of the element to the center of the aperture measured in units of cT/2.

One of ordinary skill in the art will recognize that n may be calculated in real time by a simple counter. Therefore, to obtain the arrival time $t_n$, a method is necessary to calculate $d_n$. However, direct calculation of $d_n$ using formula (4) is not practical due to the multiplication and square root operations involved.

Referring now to FIG. 2, the graph shows the relationship between the depth n along the beam axis and the distance $d_n$ for two elements of the phased array 10. The dashed line corresponds to an element at the center 12 of the aperture. The continuous line corresponds to an element 11 at a position located away from the center 12 of the phased array 10. For the center element represented by the dashed line, $d_n$=n varies linearly with n with slope S=1, whereby $d_n$ increases by 1 when n increases by 1. For the element 11 located away from the center of the aperture, $d_n$ has initially a slope less than 1, and the slope gradually increases with depth approaching 1. As is known to one of ordinary skill in the art, it is common in ultrasound imaging to begin adding an element's contribution to the ultrasound beam starting from a non-zero depth $n_f$=2f|x|, where the value of f is typically selected in the range 1 to 3 and |x| is the element's distance to the element of the center 12 of the aperture.

It has been discovered that for many array geometries commonly utilized in ultrasound imaging and for a value of f greater than or equal to 1, the slope of the $d_n$ vs. n curve is at least ⅞=1−½³. This minimum slope value may be used advantageously in the present invention to provide both high accuracy and a simple algorithm for estimating d.

A slope range of ⅞ to 1 may produce the following first algorithm of Formula 5 for estimating $d_{n+1}$ when $d_n$ is known and n>$n_f$. We denote by $â_n$ the estimate of $d_n$.

First Algorithm
Initialization (at n=nf)

$n=n_f$ $â_n=d_n$

Update (for any n>$n_f$)
if $d_n$>=$â_n$ then S=1 else S=⅞

$â_{n+1}=â_n+S$ $n=n+1$ (5)

When the d estimate grows by 1 from one depth value n to the next it may exceed the exact value of d; however, since the exact value of d may also increase by at least ⅞, the error will not be larger than the difference 1−⅞=⅛. Conversely, when the estimate grows by ⅞, the estimate may be less than the exact value of d, however since the exact value of d may not increase by more than 1 the absolute value of the error again will be less than ⅛. This results in a maximum absolute timing error less than T/16=1/64 $F_c$ and exceeds the accuracy requirements of typical ultrasound imaging systems.

Note that the first algorithm of Formula (5) differs from the prior art in which the choice of the slope (increment) S was between zero and a (constant or depth-dependent) non-zero value. The first algorithm of the present invention uses one of two non-zero slope (increment) S values for the iterative calculation of distance $d_n$.

The first algorithm of Formula (5) described above relies on the availability of the exact value $d_n$ at each depth n, which is precisely the problem we were trying to first solve. To overcome this we apply a technique known to one of ordinary skill in the art, rather than decide the slope S based on comparing the exact and estimated values of d we compare the squares of the exact and estimated values of d. However, differently than the prior art, the decision quantity (difference of the squares of the exact and estimated values) may be calculated as shown in the Equation (8) and the second algorithm of Formula (10) shown below.

By squaring both sides of equation (4) mentioned above, replacing n by n+1 and regrouping the terms we find that the square of the exact value of d can be calculated iteratively in Equation (6) as follows:

$$d_{n+1}^2 = d_n^2 + 2n + K \qquad (6)$$

$$\text{where } K = 1 - 2x \sin \theta \qquad (d1)$$

is a constant for a given beam and element.

The square of the estimate can also be calculated iteratively in Equation (7) as follows:

$$â_{n+1}^2 = â_n^2 + 2Sâ_n + S^2 \qquad (7)$$

where S is the slope=⅞ or 1, as selected in the first algorithm of Formula (5).

Since we use the 2 squared variables in Equations (6) and (7) only for decision purposes, we are only interested in iteratively calculating their difference. By conveniently grouping terms and using the equations (6) and (7), we obtain the Equation (8) as follows:

$$d_{n+1}^2 - â_{n+1}^2 = (d_n^2 - â_n^2) + (2(n - â_n) + K) + sâ_n/4 - S^2 \qquad (8)$$

where:
if $d_n$>=$â_n$ then s=0, S=1
else s=1, S=⅞ where s is the sign bit of the difference evaluated at a depth n.

In arriving at equation (8) we made use of the fact that subtracting $2Sâ_n$ when S=⅞ is equivalent to subtracting $2â_n$ and adding back $â_n/4$, operations involving only arithmetic shifts but no multiplications.

We introduce the notations:

$$D_n = d_n^2 - â_n^2 \qquad (d2)$$

$$A_n = 2(n - â_n) + K \qquad (d3)$$

and note that $A_n$ can be updated iteratively at Equation (9) as follows:

$$A_{n+1} = A_n + 2(1 - S) \qquad (9)$$

where S is ⅞ or 1 as described above.

With these modifications and notations the second algorithm for calculating $â_n$ becomes Equation (10) as follows:

Second Algorithm:
1. Initialization (at n=$n_f$)

$n=n_f$ $â_n=d_n$ $A_n=2(n-d_n)+K$ $D_n=0$

2. Update (n>$n_f$)
If $D_n \geq 0$ $D_{n+1}=D_n+A_n+â_n/4-49/64$ $A_{n+1}=A_n$ $â_{n+1}=â_n+1$ else $$D_{n+1}=D_n+A_n-1$$

$$A_{n+1}=A_n+¼$$

$$d_{n+1}=d_n+⅞$$

$$n=n+1 \qquad (10)$$

For purposes of example, the second algorithm was explained based on a minimum slope of ⅞. However, one of ordinary skill in the art recognizes that one can easily modify the algorithm to operate with other minimum slope values of the form $1-½^i$ where i=0, 1, 2 . . . , and preferably i=3. For example, the modifications may involve changes in the constants used in the second algorithm. Thus, if values of f greater than 1.4 are acceptable then a minimum slope of ¹⁵⁄₁₆ may be used and provide further the benefit of reduced error. In the alternative, a minimum slope value of ¾ may also produce adequately small errors and allow smaller values of f. Minimum slopes of form other than $1-½^i$ may also be used; however, alternative minimum slopes may complicate the implementation of the second algorithm. It is also noted that the maximum error is proportional with T and therefore can be further reduced by increasing the sampling frequency F.

Referring now to FIG. 4, a circuit 200 for implementing the second algorithm is shown. The figure is a simplified representation of a circuit, showing only the data path and omitting the timing and control signals as known to one of ordinary skill in the art. One of ordinary skill in the art will also recognize that overall circuit complexity may be simplified as some of the multiplexers may be incorporated in the same physical circuit as the arithmetic units they feed, for example, when the circuit is implemented with look-up table field programmable gate arrays. Before the start of a beam, multiplexers 212 and 221 may be controlled to pass the initialization values $A_{nf}$ and $d_n$ respectively (where $n=n_f$) and adders 213 and 223 may be controlled to pass these initialization values unmodified to the registers 214 and 224, respectively. At the same time, register 236 may be cleared initializing the decision quantity $D_n$ to 0. The circuit may then estimate $d_n$ at the sampling clock speed, that is, one estimate per clock, for all depths larger than $n_f$.

During execution of the second algorithm using circuit 200, the most significant (sign) bit of $D_n$ may be used in the control logic (not shown) to select the slope S as specified by the second algorithm. For example when that bit is 0 the gates 211 are disabled; the multiplexer 222 is controlled to pass the slope value 1; the gates 233 are disabled; and, the multiplexer 232 is controlled to pass the squared slope ($S^2$) value 1. The division $d_n/4$ is an arithmetic shift achieved simply by the wiring of output bits of register 224 to the inputs of the gates 233. The logic format used in circuit 200 may be integer(s), with the decimal part of the numbers represented by the least significant bits of the integers. Preferably, three (3) least significant bits are used to represent the decimal part, but a larger number of bits may be used depending on the application and accuracy requirements as is understood by one of ordinary skill in the art. The number of most significant bits, representing the integer part of the various quantities, varies depending upon the maximum number of depth positions. Preferably, typical medical ultrasound systems component 211 has 1 bit (with all other bits hard-wired), components 212, 213 and 214 each have 14 bits, component 222 has 4 bits (with all other bits hard-wired), component 232 has 4 bits (with all other bits hard-wired), and the other components each have 16 bits, and for all these components the least significant three (3) bits represent the decimal part of the respective quantities.

While the circuit 200 of FIG. 4 was described as the preferred embodiment of the second algorithm, it will be obvious to one of ordinary skill in the art that the second algorithm may be implemented by other circuits or as a program executed on a computer embedded in a medical ultrasound system. In particular, if the circuit 200 is operated at clock frequencies greater than the ultrasound sampling rate, then fewer arithmetic units than those shown in FIG. 4 may be used in a time-multiplexed fashion, with at least one arithmetic unit performing more than one of the arithmetic operations of the algorithm as is recognized and understood by one of ordinary skill in the art.

To this point only method(s) for estimating the distance d of FIG. 1 has been described. However, the method(s) of the present invention may be employed in ultrasound receive beamformers. Referring now to FIG. 3, a block diagram of a typical receive beamformer 30 is shown. Receive beamformer 30 may comprise multiple channels 31, a summer 32 and an initialization controller 33. Referring now to FIG. 3a, the general structure of a channel of FIG. 3 is shown. The channel 31 may comprise a delay block 36 and a delay controller 38. Prior to beam transmission, the initialization controller 33 initializes each channel's delay controller according to the beam characteristics, e.g., steering angle, array geometry and position in aperture of the element connected to the channel. After beam transmission occurs, echoes may begin arriving at the array elements. The echoes may be converted into electrical signals, preprocessed, e.g., amplified and filtered, and the preprocessed electrical signals may be fed into the inputs of the beamformer channels 31. The delay blocks 36 may further process and delay the signals under the control of delay controllers 38, such that the signals arrive phase-aligned at the inputs of the summer 32, where the signals are summed to form the beamformed signal.

The second algorithm of the present invention may be incorporated by means, for example, of circuit 200 or a variant of circuit 200 as recognized by one of ordinary skill in the art, in the delay controller 38, where the second algorithm may be used in a manner dependent on the particular method of implementing the delay block 36 as known to one of ordinary skill in the art. For example, the delay block 36 may comprise an arrangement of analog delay lines and analog multiplexers to provide a coarse delay, or may be combined with analog mixers to provide fine phase delay. In another example of an implementation of the method of the present invention, the delay block 36 may contain an analog to digital converter (not shown) to convert the electrical signal into its numerical representation, a memory storage unit (not shown) which provides coarse delay at the resolution of the sampling period, and an interpolator (not shown) to provide fine delay, e.g., subsample. In yet another implementation of the method of the present invention, an analog to digital converter's clock may be phase-modulated to provide the fine delay and the digital signals may then be written to a memory storage unit (not shown) which provides the coarse delay. Such converters, memory storage units and interpolators are well known to those of ordinary skill in the art and are well described in both technical literature and numerous patents. The control signals generated by delay controller 38 may generally be one of three types: delay (δ), arrival time (t), or the sign of the decision quantity $D_n$. The sign of the decision quantity $D_n$ may be obtained directly from the execution of the second algorithm using circuit 200. The calculation of the other control signals, that is, delay (δ) and arrival time (t), will now be explained in greater detail.

Referring again to FIG. 1, the delay 6 of the echo to a lateral element relative to the center of the aperture is shown in Equation (11):

$$\delta = (d-r)/c \qquad (11)$$

or, with the time and distance units defined before, as shown in Equation (12):

$$\delta_n < (d_n - n)/2 \qquad (12)$$

To compensate the delays, the negative values of the delays may be applied to the signals, and may be offset by a constant $C_1$ applied to all channels in order to make the physical delays positive. The delay controller 38 therefore has to generate the control signal shown in Equation (13):

$$del_n = C_1 - d_n/2 + n/2 \qquad (13)$$

Figure 5:
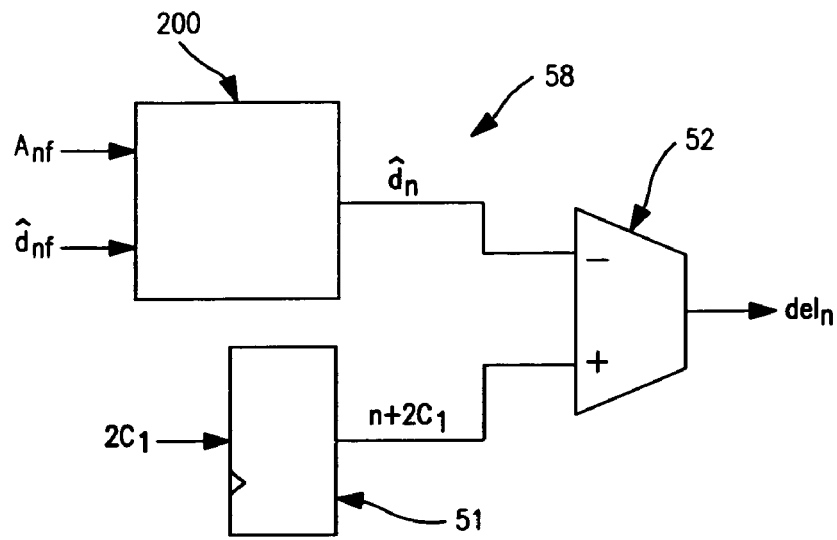
FIG. 5 shows the block diagram of a delay controller incorporating the method of the invention.

This can be obtained with a delay controller 58 of FIG. 5. The delay controller 58 may comprise the circuit 200 of FIG. 4 that implements the second algorithm of the present invention, a depth counter 51, a subtractor 52 and a timing/control block (not shown). The depth counter 51 is preset to $2C_1$ before the start of the beam and then increments at each sampling clock. The divisions by 2 of equation (13) are performed by selecting the appropriate bits. The circuit may be further simplified by using a single depth counter 51 for multiple delay controllers 38. The arrival time calculation is shown in the aforementioned Equation (3) described above. For implementation reasons sometimes a constant $C_2$ may be added to Equation (13), and the implementation of the delay controller 38 of FIG. 3a may be similar to the delay controller 58 shown in FIG. 5 and described above except that the subtractor block 52 may be replaced with an adder as understood by one of ordinary skill in the art.

As described above, the beamformer 30 operation may begin with an initialization performed by initialization controller 33. Each channel's delay controller 38 may require an initial value for the variables $A_n$ and $d_n$ as well as the initial depth value $n_f$ at which the channel 31 may be activated. For a 128-element phased array and 128 steering angles this requires 64×3×128 parameters, where the symmetry of the steering angles was used to reduce the number of parameters by a factor of 2. Rounding up to a power of 2 results in a memory requirement of 32 KWords per probe. This memory requirement may represent a considerable cost especially in low-end portable ultrasound systems or in other compact ultrasound system designs where space and power are scarce. Other disadvantages are present such as long dead time when switching from one transducer probe to another which requires loading new parameter tables.

Figure 6:
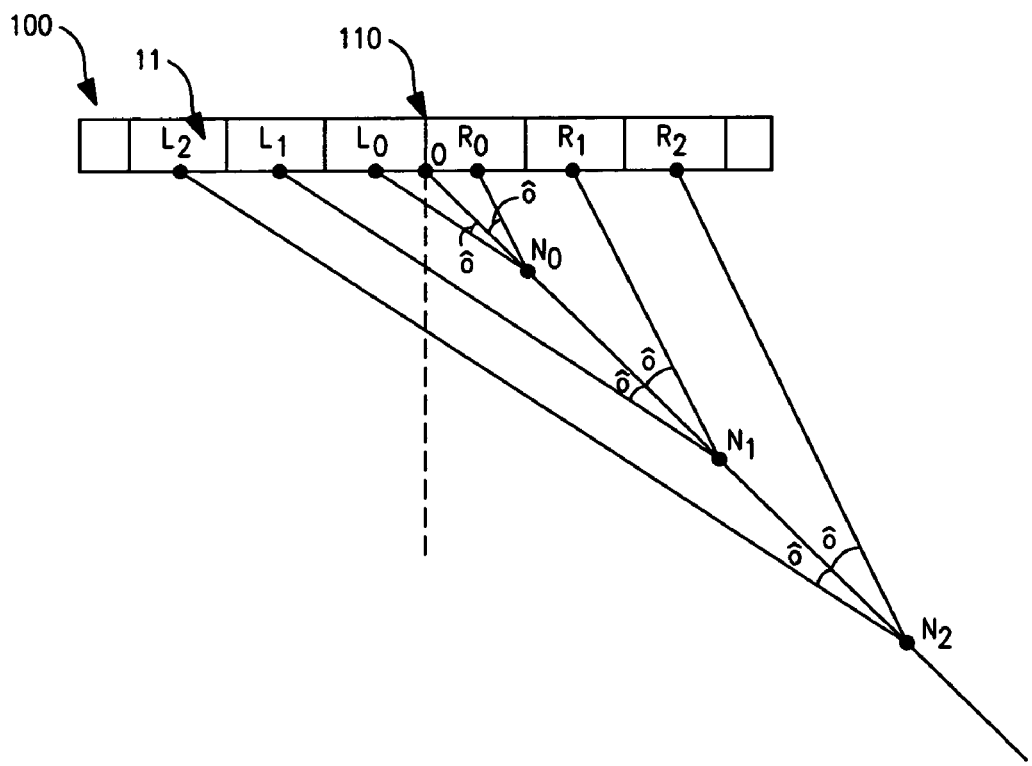
FIG. 6 shows the geometry at the initial depth for several array elements.

Referring now to FIG. 6, to reduce the number of parameters we may take advantage of the geometry at depth $n = n_f$ for various elements. FIG. 6 shows the first 3 elements to the left (and their centers $L_i$ where i=0, 1, . . . ) and the first 3 elements to the right (and their centers $R_i$ where i=0, 1, . . . ) of a center 110 (hereinafter referred to as the capital letter "O") of a phased array 100, including a beam axis 112 and at least one point $N_i$ indicating a depth $n_{fi}$. The points indicating depths $n_{fi}$ are equivalent for the elements which are symmetrical versus the center of the aperture by the definition of $n_{fi}$ as indicated in Equation (14):

$$n_{fi} = 2f^*OL_i = 2f^*OR_i = ON_i \qquad (14)$$

Referring again to FIG. 1 and definitions described above, the following Equations (15), (16) and (17) may be observed for an element i (i=0, 1, . . . ) to the left of the array center 110 as follows:

$$OL_i = x_i \qquad (15)$$

$$ON_i = n_{fi} = 2f|x_i| = 2f^*OL_i \qquad (16)$$

$$L_i N_i = d_{nfi} \qquad (17)$$

Triangles $OL_i N_i$ and $OL_j Nj$ have the angle Ô in common and by equations (15) and (16) $OL_i/OL_j = ON_i/On_j = x_i/x_j$; therefore, the two triangles are similar; and, therefore from Equation (17) $d_{nfi}/d_{nfj} = L_i N_i/L_i N_j = x_i/x_j$. Therefore, both $n_{fi}$ and $d_{nfi}$ grow proportionally to their distance $|x_i|$ from the origin of the beam. This now provides a method to calculate the two parameters $n_{fi}$ and $d_{nfi}$ for each left element starting from their value for the left element 0 ($n_{f0}$ and $d_{nf0}$) and their increments $\Delta n_f$ and $\Delta d_{nf}$ from element to element. In order to guarantee integer sampling positions, $n_{f0}$ is rounded (causing small departures of f from the exact specified value) and considering that $x_0$ is half of the distance, that is, the pitch, between elements we have Equations (18) and (19):

$$\Delta n_f = 2 n_{f0} \qquad (18)$$

$$\Delta d_{nf} = d_{nf1} - d_{nf0} \qquad (19)$$

where $d_{nf1}$ and $d_{nf0}$ are calculated in Equations (20) and (21) according to Equation (4).

$$n_{fi} = n_{f0} + i \times \Delta n_f \qquad (20)$$

$$d_{nfi} = d_{nf0} + i \times \Delta d_{nf} \qquad (21)$$

The expression $K_i$, according to its definition (d1) of Equation (6), varies proportionally with the signed value of $x_i$ and can be calculated in a similar manner according to Equation (22):

$$K_i = K_0 - i \times \Delta K \qquad (22)$$

where $\Delta K = -2 \times pitch \times \sin \theta$ $A_{ni}$ is then obtained by its definition (d3) from $n_{fi}$, $d_{nfi}$ and $K_i$.

The same methods may apply to the elements to the right of the array, that is, $R_i$ where i=0, 1, . . . . It should be noted that for the symmetrical aperture described herein $n_{f0}$ and $\Delta n_f$ are the same on the left and right sides of the phase array 100, but $d_{nf0}$ and $\Delta d_{nf}$ are different when the steering angle is a value other than 0. It should also be noted that that for the right side $K_0$ and $\Delta K$ are the same as for the left side. However, when implementing the right side $K_0$ and $\Delta K$, Equation (22) takes on a slightly different form as Equation (22'):

$$K_i = K_0 + (i+1) \times \Delta K \qquad (22')$$

Therefore, only eight (8) parameters are needed for each steering direction irrespective of the number of elements present in the phase array. For the previous example of the 128-element phased array and 128 steering angles this results in a total memory size of 64×8=0.5 Kword. Due to symmetry only 128/2=64 sets of parameters are required. Therefore, a 64-fold reduction in memory at the expense of an additional arithmetic circuit is recognized. The implementation of the second algorithm in ultrasound receive beamformers is advantageous when the initialization controller is implemented with a technology such as a field programmable gate array, where logic and arithmetic units are readily available and inexpensive but memory is relatively scarce.

The parameter table size can be further reduced by taking advantage of the fact that the pitch ($\Delta x$) is equivalent to double the distance $x_0$ for the first left/right elements. Considering that, as shown before, the parameters of interest vary from element to element in proportion to the element's position x, it follows that the initial parameter values may be calculated from the increments shown in Equations (23)-(25) as follows:

$$n_{f0} = \Delta n_f/2 \quad (23)$$

$$d_{nf0} = \Delta d_{nf}/2 \quad (24)$$

$$K_0 = 1 - \Delta K/2 \quad (25)$$

Note that for the elements on the right side of the phase array 100, $\Delta d_{nf}$ may be different than for the elements on the left side, and $K_0$ may be calculated with an adder instead of a subtractor as shown in Equation (25') as follows:

$$K_0 = 1 + \Delta K/2 \quad (25')$$

Therefore, only the increments are needed in the initialization tables, reducing the memory requirement by another factor of 2 to 256 words or a total reduction by a factor of 128.

In some implementations of the initialization algorithm, that is the second algorithm, of the present invention, multipliers are readily available and the calculation of initialization parameters may be performed using equations (20), (21), (22) directly. Multipliers however are generally expensive. In order to avoid calculations involving multiplication, equations (20), (21) and (22) may be replaced with a third algorithm of Formula (26) which calculates the initialization parameters iteratively, by repeatedly adding the increments $\Delta n_f$, $\Delta d_{nf}$, $\Delta K$ to the respective parameters:

Third Algorithm:
1. Set up for first left element
Load increment registers $\Delta n_f$, $\Delta d_{nf}$, $\Delta K$
Load accumulators with first left element values $$n_{fi} = \Delta n_{f0}/2 \quad (26)$$

$$d_{nfi} = \Delta d_{nf0}/2$$

$$K_i = 1 - \Delta K/2$$

Calculate first left value of An $$A_{nfi} = 2(n_{fi} - d_{nfi}) + K_i$$

2. Iterative calculation for all left elements after first $$n_{fi} = n_{fi} + \Delta n_f$$

$$d_{nfi} = d_{nfi} + \Delta d_{nf}$$

$$K_i = K_i - \Delta K$$

$$A_{nfi} = 2(n_{fi} - d_{nfi}) + K_i$$

3. Set up for first right element
Load increment registers $\Delta n_f$, $\Delta d_{nf}$, $\Delta K$
Load accumulators with first right element values $$n_{fi} = \Delta n_{f0}/2$$

$$d_{nfi} = \Delta d_{nf0}/2$$

$$K_i = 1 + \Delta K/2$$

Calculate first left value of An $$A_{nfi} = 2(n_{fi} - d_{nfi}) + K_i$$

4. Iterative calculation for all right elements $$n_{fi} = n_{fi} + \Delta n_f$$

$$d_{nfi} = d_{nfi} + \Delta d_{nf}$$

$$K_i = K_i + \Delta K$$

$$A_{nfi} = 2(n_{fi} - d_{nfi}) + K_i \quad (26)$$

While the method of calculating initialization parameters has been explained by means of equations (20), (21), (22) and the iterative initialization algorithm, that is, the third algorithm, of Formula (26) above, it will be obvious to one skilled in the art that alternative formulations based on the proportionality principle of the present invention may be conceived and practiced.

Figure 7:
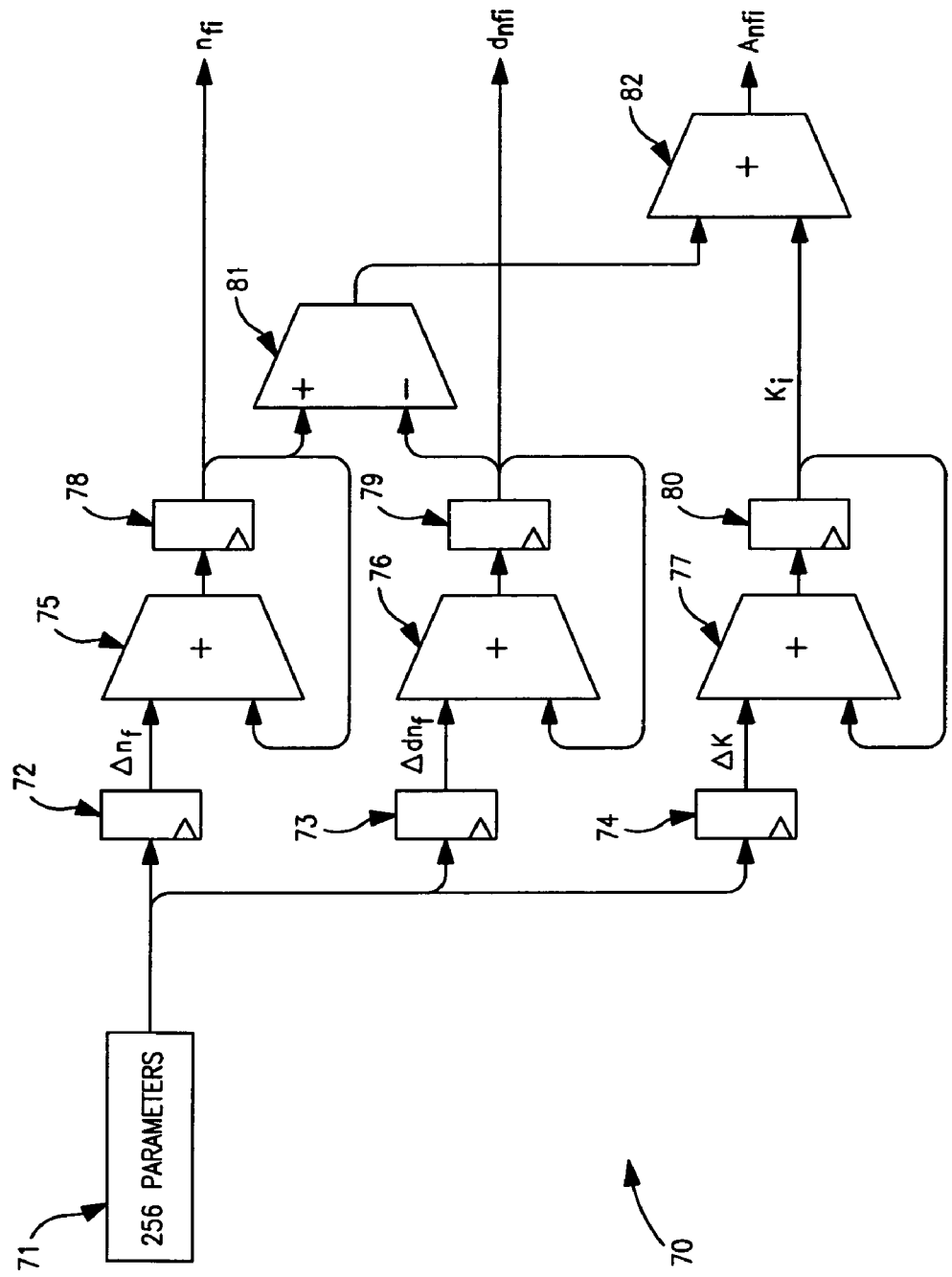
FIG. 7 shows a circuit which calculates the initialization parameters according to the method of the invention.

Referring now to FIG. 7, a circuit 70 is shown which may implement the iterative initialization algorithm of Formula (26). Circuit 70 represents a simplified schematic diagram showing only the parameter memory, registers and arithmetic units and omitting the timing and control circuits and signals as recognized by understood by one of ordinary skill in the art. During the setup phases 1 and 3 of the iterative initialization algorithm of Formula (26), the increments may be read from a parameter memory 71 and loaded into a plurality of shift registers 72, 73 and 74. At the same time, accumulator registers 78 and 79 may be reset to 0 and accumulator register 80 may be preset to 1. Next, shift registers 72, 73 and 74 may downshift by one bit to divide the increments by 2 and then the initial values of the accumulator registers 78, 79, 80 may be calculated according to equations (23), (24), (25) and (25') respectively. Afterwards, the shift registers may shift up by one bit to restore the increment values. The circuit 70 may then proceed to perform the iterative calculation phases 2 and 4 of the iterative initialization algorithm of Formula (26). Arithmetic units 75, 76 and 77 may perform the first three (3) operations of steps 2 and 4 of the initialization algorithm. Arithmetic units 75, 76 may comprise adders, and arithmetic unit 77 may comprise an adder/subtractor. For example, adder 75 repeatedly adds $\Delta n_f$ to the value of $n_{fi}$ to obtain the respective value for the next element further away from the center of the aperture. Subtractor 81 and adder 82 may calculate the $A_n$ quantity. While this circuit is particularly suitable for implementation in a field programmable gate array integrated circuit, it will be obvious to one skilled in the art that the iterative initialization algorithm of the present invention may be implemented with other circuits known to one of ordinary skill in the art or as a computer implemented program executed on a computer separate from or embedded within an ultrasound system, ultrasound system component, e.g., an ultrasound scanner, and the like.

The arrival time/delay calculation algorithm and initialization algorithm of the present invention have been described for a 1D (one-dimensional) phased array transducer, and for a scanning geometry in which the beam axis originates from the center of the aperture. However the algorithms may be extended to other configurations as understood by one of ordinary skill in the art, some of which will be briefly discussed below.

In some situations it is desirable to produce beams whose axis originates at different positions on the aperture than its center. In such cases, the value x of the position of the various elements has to be measured against the origin of the beam instead of the center of the aperture, but the equations used in this disclosure except (18), (23), (24), (25), (25') remain valid. Therefore, the delay/arrival time algorithms remain valid. The initialization algorithm based on proportionality also remains valid except for the portions dependent on the beam origin being halfway between two elements. Thus, if the origin of the beam is not exactly halfway between two elements then nfo will take different values to the left and right of the origin of the beam, therefore one extra initialization parameter will be needed. Likewise the calculation of the first left/right parameters from the increments is no longer so simple and it may be more convenient to increase the size of the table to include both the first left/right values and the increments. If the distance from the beam origin to the closest element center is of the form pitch/$2^i$ then the initialization algorithm and its implementation with circuit 70 can still be used with small modifications which will be obvious to one skilled in the art.

The arrival time/delay calculation algorithm based on second algorithm also applies to convex, e.g., curvilinear, arrays when the steering angle θ is 0, that is, no steering, with the following modification of definition (d1) which does not affect the second algorithm formulation:

$$K\text{convex}=1+2R(1-\cos\phi) \quad (\text{d1-convex})$$

where R is the radius of the convex array and φ is the angular position of the element's center relative to the beam axis.

For the convex array initialization parameters are calculated based on the array's curvilinear geometry, and the method to derive all elements' parameters from initial values and increments no longer applies.

Finally, second algorithm may be extended to include 1.5-dimensional, 1.75-dimensional and 2-dimensional arrays. Indeed, consider an element in the plane of the array and a beam steered at some azimuth and elevation angles and with the origin in the plane of the array. If we construct a plane containing the beam axis and the center of the element, then the beam origin and the beam axis will exhibit the same geometric relationships in that plane as the geometry shown in FIG. 1 and may also be used to derive the arrival time/delay calculation algorithms using the second algorithm of the present invention. Initialization parameters may then have to be calculated differently than described for the phased array as will be recognized by one of ordinary skill in the art.

One or more embodiments of the present invention have been described. Nevertheless, it will be understood that various modifications may be made without departing from the spirit and scope of the invention. Accordingly, other embodiments are within the scope of the following claims.

What is claimed is:

1. In an ultrasound imaging system comprising an ultrasound transducer having an array of elements and a beam origin, each element for converting received energy into an echo signal, a process comprising the steps of:
    calculating an integer-valued depth (n), said depth (n) measured from said beam origin to a point on a beam axis of an ultrasound beam;
    estimating a distance ($\hat{d}_n$) representative of the exact distance ($d_n$) measured from a center of an element to said point on said beam axis;
    adding said estimated distance ($\hat{d}_n$) to said integer-valued depth (n) to generate an arrival time control signal or subtracting said estimated distance ($\hat{d}_n$) from said integer-valued depth (n) to generate a delay control signal; and
    processing an echo signal associated with said element based on the arrival time control signal or the delay control signal.

2. The process of claim 1, wherein the calculation step comprises comparing a square of an exact value of said distance ($d_n$) to a square of an estimated value of said distance ($\hat{d}_n$) according to an equation:

$$d_{n+1}^2 - \hat{d}_{n+1}^2 = (d_n^2 - \hat{d}_n^2) + (2(n-\hat{d}_n)+K) + s\hat{d}_n/4 - S^2$$

wherein (n) is said depth from said beam origin to a point along said beam axis, wherein K=1−2x sin θ, wherein θ is a steering angle of said beam axis relative to a vertical axis of said array, wherein S is a slope of said distance with respect to said depth (n), and wherein s is a sign bit of a difference shown in the equation, evaluated at said depth (n).

3. The process of claim 2, wherein the comparison step comprises:
    determining that said exact value of said distance ($d_n$) is greater than or equal to said estimated value of said distance ($\hat{d}_n$);
    based on the determination, setting said s equal to a value of zero; and
    based on the determination, setting said slope S equal to a value of one.

4. The process of claim 2, wherein the comparison step comprises:
    determining whether said exact value of said distance is greater than or equal to said estimated value of said distance;
    determining that said exact value of said distance ($d_n$) less than said estimated value of said distance ($\hat{d}_n$);
    based on the determination, setting said s equal to a value of one; and
    based on the determination, setting said slope S equal to a value of ⅞.

5. The process of claim 1, wherein the calculation step comprises comparing a square of an exact value of said distance ($d_n$) to a square of an estimated value of said distance ($\hat{d}_n$) according to an equation:

$$d_{n+1}^2 - \hat{d}_{n+1}^2 = (d_n^2 - \hat{d}_n^2) + (2(n-\hat{d}_n)+K) + s\hat{d}_n/2^{i-1} - S^2$$

wherein (n) is said depth from said beam origin to a point along said beam axis, wherein K=1−2x sin θ, wherein θ is a steering angle of said beam axis relative to a vertical axis of said array, wherein S is a slope having a value according to an equation 1−½$^i$, and wherein s is equal to a value of one.

6. The process of claim 5, wherein the comparison step comprises:
    determining that said exact value of said distance ($d_n$) is less than said estimated value of said distance ($\hat{d}_n$); and
    based on the determination, setting said s to said value of one and said slope S to said value according to said equation 1−½$^i$.

7. The process of either claim 1 or claim 2, wherein said transducer is a curvilinear array and the calculation step further comprises comparing a square of an exact value of said distance ($d_n$) to a square of an estimated value of said distance ($\hat{d}_n$) according to an equation:

$$d_{n+1}^2 - \hat{d}_{n+1}^2 = (d_n^2 - \hat{d}_n^2) + (2(n-\hat{d}_n)+K) + s\hat{d}_n/4 - S^2$$

wherein (n) is said depth from said beam origin to a point along said beam axis, wherein S is said slope, wherein s is a sign bit, wherein K=1+2R(1−cos φ), wherein R is a radius of a convex array, φ is an angular position of said center of said element relative to said beam axis and a steering angle θ=0.

8. An ultrasound system, comprising:
    an ultrasound transducer comprising an array of elements and a beam origin, each of said elements for converting received energy into an echo signal; and
    a beamformer comprising:
    an initialization controller including initialization controller circuitry for calculating initialization parameters;
    at least one channel including a delay circuit and a delay controller for:

calculating an integer-valued depth (n), said depth (n) measured from said beam origin to a point on a beam axis of an ultrasound beam;

estimating a distance ($\hat{d}_n$) representative of the exact distance ($d_n$) measured from a center of an element to said point on said beam axis;

adding said estimated distance ($\hat{d}_n$) to said integer-valued depth (n) to generate an arrival time control signal or subtracting said estimated distance ($\hat{d}_n$) from said integer-valued depth (n) to generate a delay control signal; and processing an echo signal associated with said element based on the arrival time control signal or the delay control signal; and a summer for summing processed echo signals to form a beamformed signal.

9. The ultrasound system of claim 8, wherein said delay controller includes delay controller circuitry for estimating the distance ($\hat{d}_n$) at a sampling clock speed, said delay controller circuitry comprising:

a first gate and at least one first multiplexer for receiving and passing at least one initialization value to at least one first adder;

at least one first register for receiving and passing said at least one initialization value to a second adder;

at least one second register for receiving and passing said at least one initialization value through a second gate to an adder/subtractor;

at least one second multiplexer for passing a squared slope value to said adder/subtractor;

at least one third adder for receiving said at least one initialization value from said second adder and said adder/subtractor; and at least one third register for receiving said at least one initialization value.

10. The ultrasound system of claim 9, wherein said at least one first multiplexer comprises a multiplexer for passing an $A_{nf}$ initialization value, a multiplexer for passing an estimated depth $\hat{d}_n$, and a multiplexer for passing a slope S initialization value.

11. The ultrasound system of claim 9, wherein said at least one first register comprises a register to pass an $A_n$ initialization value and a register to pass a $\hat{d}_n$ initialization value.

12. The ultrasound system of claim 9, wherein said delay computation circuitry comprises means for updating a previous delay computed for a previous depth by at least one update value.

13. The ultrasound system of claim 8, wherein said delay is an estimated delay with respect to a reference delay of an echo signal from an array center element.

14. The ultrasound system of claim 8, wherein said ultrasound transducer comprises an array selected from the group consisting of a phased array, a linear array, a two-dimensional array, and a curvilinear array.

15. In an ultrasound imaging system comprising an ultrasound transducer having an array of elements and a beam origin located between two adjacent elements, each element for converting received energy into an echo signal, a process for calculating initialization parameters from a reduced parameter table, the process comprising the steps of:

setting at least one increment value for at least one initialization parameter for a first left element located to the left of said beam origin and a first right element located to the right of said beam origin;

storing in a memory storage device said at least one increment for said first left element and said first right element;

calculating said at least one initialization parameter for at least one beam steering angle for said first left element and for said first right element;

storing in said memory storage device said at least one initialization parameter for said first left element and said first right element; and calculating at least one additional initialization parameter for said at least one beam steering angle for at least one next left element located to the left of said first left element and for at least one next right element located to the right of said first right element based upon the stored said at least one initialization parameter for said first left element and said first right element.

16. The process of claim 15, wherein said at least one initialization parameter comprises the following: an initial depth ($n_{fi}$), an initial distance ($d_{nfi}$) measured from a center of an element to a point at said initial depth, and an initial quantity calculated according to an equation $A_{nfi}=2(n_{fi-dnfi})+K_i$, wherein $K_i=1-2x_i \sin\theta$, $\theta$ is a beam steering angle, and x is a distance measured from a center of said element to said beam origin.

17. The process of claim 15, wherein said at least one increment comprises the following: an initial distance increment ($\Delta d_{nfL}$) for said first left element, an initial distance increment ($\Delta d_{nfR}$) for said first right element, an initial depth increment ($\Delta n_f$) for both said first left element and said first right element, and a K increment ($\Delta K$) for both said first left element and said first right element, wherein said initial depth ($n_{f0L}$) for said first left element and said initial depth ($n_{f0R}$) for said first right element are proportional to a distance (x) measured from a center of said first left element or said first right element to said beam origin.

18. The process of claim 15, wherein the storing step further comprises:

storing an initial distance increment ($\Delta d_{nfL}$) for said first left element;

storing an initial distance increment ($\Delta d_{nfR}$) for said first right element;

storing an initial depth increment ($\Delta n_f$) for both said first left element and said first right element; and storing a K increment ($\Delta K$) for both said first left element and said first right element.

19. The process of claim 18, wherein the calculation of said at least one initialization parameter step further comprises:

calculating an initial depth ($n_{f0L}$) for said first left element according to an equation $n_{f0L}=\Delta n_f/2$;

calculating an initial distance ($d_{nf0L}$) for said first left element according to an equation $d_{nf0L}=\Delta d_{nf0L}/2$;

calculating a quantity $K_{0L}$ for said first left element according to an equation $K_{0L}=1-\Delta K/2$;

calculating an initial depth ($n_{f0R}$) for said first right element according to an equation $n_{f0R}=\Delta n'/2$;

calculating an initial distance ($d_{nf0R}$) for said first right element according to an equation $d_{nf0R}=\Delta d_{nf0R}/2$; and calculating a quantity $K_{0R}$ for said first right element according to an equation $K_{0R}1+\Delta K/2$, wherein said initial depth ($n_{f0L}$) for said first left element and said initial depth ($n_{f0R}$) for said first right element are proportional to a distance (x) measured from a center of said first left element or said first right element to said beam origin, wherein a distance (x) measured from a center of said first left element to said beam origin is equivalent to said distance (x) measured from a center of said first right element to said beam origin.

20. The process of claim 15, wherein the storing step further comprises:
   storing an initial depth ($n_{f0L}$), an initial distance ($d_{nf0L}$), a quantity $K_{0L}$, an initial distance increment ($\Delta d_{nfL}$) for said first left element;
   storing an initial depth ($n_{f0R}$), an initial distance ($d_{nf0R}$), a quantity $K_{0R}$, an initial distance increment ($\Delta d_{nfR}$),
   storing an initial depth increment ($\Delta n_f$) for both said first left element and said first right element; and
   storing a K increment ($\Delta K$) for both said first left element and said first right elements,
   wherein said initial depth ($n_{f0L}$) for said first left element and said initial depth ($n_{f0R}$) for said first right element are proportional to a distance (x) measured from a center of said first left element or said first right element to said beam origin.

21. The process of claim 15 wherein the calculation of said at least one additional initialization parameter step further comprises:
   calculating a next initial depth ($n_{f0L}$) for said at least one next left element according to an equation $n_{fi}=n_{f0L}+i\times\Delta n_f$;
   calculating a next initial distance ($d_{nf0L}$) for said at least one next left element according to an equation $d_{nfi}=d_{nf0L}+i\times\Delta d_{nfL}$;
   calculating a next quantity $K_{0L}$ for said at least one next left element according to an equation $K_i=K_{0L}-i\times\Delta K$;
   calculating a next initial depth ($n_{f0R}$) for said at least one next right element according to an equation $n_{fi}=n_{f0R}+i\times\Delta n_f$;
   calculating a next initial distance ($d_{nf0R}$) for said at least one next right element according to an equation $d_{nfi}=d_{nf0R}+i\times\Delta d_{nfR}$; and
   calculating a next quantity $K_{0R}$ for said at least one next right element according to an equation $K_i=K_{0R}+i\times\Delta K$,
   wherein said next initial depth ($n_{f0L}$) for said at least one next left element and said next initial depth ($n_{f0R}$) for said at least one next right element are proportional to a distance (x) measured from a center of said first left element or said first right element to said beam origin.

22. The process of claim 15, wherein the calculation of said at least one additional initialization parameter step further comprises:
   calculating a next initial depth ($n_{f0L}$) for said at least one next left element according to an equation $n_{fi}=n_{f(i-1)L}+\Delta nf$;
   calculating a next initial distance ($d_{nf0L}$) for said at least one next left element according to an equation $d_{nfi}=d_{nf(i-1)L}+\Delta d_{nfL}$;
   calculating a next quantity $K_{0L}$ for said at least one next left element according to an equation $K_i=K_{(i-1)L}-\Delta K$;
   calculating a next initial depth ($n_{f0R}$) for said at least one next right element according to an equation $n_{fi}=n_{f(i-1)R}+\Delta n_f$;
   calculating a next initial distance ($d_{nf0R}$) for said at least one next right element according to an equation $d_{nfi}=d_{nf(i-1)R}+\Delta d_{nfR}$; and
   calculating a next quantity $K_{0R}$ for said at least one next right element according to an equation $K_i=K_{(i-1)R}+\Delta K$,
   wherein said next initial depth ($n_{f0L}$) for said at least one next left element and said next initial depth ($n_{f0R}$) for said at least one next right element are proportional to a distance (x) measured from a center of said first left element or said first right element to said beam origin.

23. The process of claim 15, wherein said at least one beam steering angle comprise at least one pair of beams that are symmetrical.

24. An ultrasound system, comprising:
   an ultrasound transducer comprising an array of elements and a beam origin located between two adjacent elements, each of said elements for converting received energy into an echo signal; and
   a beamformer comprising:
   an initialization controller including initialization controller circuitry for:
      setting at least one increment value for at least one initialization parameter for a first left element located to the left of said beam origin and a first right element located to the right of said beam origin;
      storing in a memory storage device said at least one increment for said first left element and said first right element;
      calculating said at least one initialization parameter for at least one beam steering angle for said first left element and for said first right element;
      storing in said memory storage device said at least one initialization parameter for said first left element and said first right element; and
      calculating at least one additional initialization parameter for said at least one beam steering angle for at least one next left element located to the left of said first left element and for at least one next right element located to the right of said first right element based upon the stored said at least one initialization parameter for said first left element and said first right element;
   at least one channel to receive the at least one initialization parameter and the at least one additional initialization parameter, each of the at least one channels including a delay circuit and a delay controller; and
   a summer for receiving a signal from each of the at least one channels and for summing the signals to form a beamformed signal.

25. The ultrasound system of claim 24, wherein said initialization controller circuitry comprises:
   said memory storage device having a plurality of increments from at least one element of said array;
   at least one shift register for receiving said plurality of increments from said memory storage device and for downshifting and dividing each of said increments to generate a plurality of shift register output;
   at least one accumulator register for receiving said shift register output and calculating a plurality of initial parameter values; and
   at least one subtractor and at least one adder for receiving said plurality of initial parameter values and for performing iterative calculations to generate at least one initialization parameter for each of said at least one elements.

26. The apparatus of claim 25, wherein said at least one shift register for downshifting each of said increments downshifts by 1 and divides by 2 each of said increments.

27. The apparatus of claim 25, wherein said increments comprise the following: $\Delta n_f$, $\Delta d_{nf}$, and $\Delta K$.

28. The apparatus of claim 25, wherein said at least one subtractor and said at least one adder for performing iterative calculations uses arithmetic shifts.

* * * * *